United States Patent [19]

Nelson

[11] 4,187,293
[45] Feb. 5, 1980

[54] STABILIZATION OF SOLUTIONS CONTAINING ACTIVE CHLORINE

[75] Inventor: G. Douglas Nelson, Creve Coeur, Mo.

[73] Assignee: Monsanto Company, St. Louis, Mo.

[21] Appl. No.: 954,700

[22] Filed: Oct. 25, 1978

[51] Int. Cl.² ............................................. A01N 11/02
[52] U.S. Cl. .................................... 424/149; 424/174; 424/175
[58] Field of Search ............... 424/149, 162, 174, 175; 252/541

[56] References Cited

U.S. PATENT DOCUMENTS

| | | | |
|---|---|---|---|
| 2,988,471 | 6/1961 | Fuchs et al. | 424/149 |
| 3,170,883 | 2/1965 | Owen et al. | 424/149 |
| 4,088,611 | 5/1978 | Suzuki et al. | 252/89 R |

*Primary Examiner*—V. D. Turner
*Attorney, Agent, or Firm*—S. M. Tarter; E. P. Grattan; P. D. Matukaitis

[57] ABSTRACT

A method of stabilizing an aqueous solution containing active chlorine against the loss of active chlorine upon exposure to ultraviolet light or by contact with aluminum, copper or iron which comprises introducing into the solution a stabilizing amount of a radical represented by the structure:

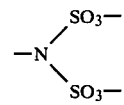

9 Claims, No Drawings

STABILIZATION OF SOLUTIONS CONTAINING ACTIVE CHLORINE

BACKGROUND OF THE INVENTION

1. Field of the Invention

This invention relates to the stabilization of aqueous solutions containing active chlorine to reduce the loss of the active chlorine upon exposure to ultraviolet light or by contact with metals.

2. Description of the Prior Art

Various sources of active chlorine have been widely used to kill pathogenic bacteria and to prevent their growth in potable water supplies and in swimming pools, and in general in sterilizing solutions. A serious drawback in the use of active chlorine as a bactericide is that the active chlorine in an aqueous solution is subject to rapid decomposition upon exposure to ultraviolet light, for example, upon exposure to sunlight, and also when in contact with metals such as iron, copper or aluminum which may be present in the equipment handling the solution. The rate of decomposition is particularly high in the very dilute solutions used in potable water supplies and swimming pools. In swimming pools, for example, where it is desired to maintain an active chlorine content of about 0.4 to 5.0 parts per million (ppm), it is generally necessary to add many times this amount of active chlorine in the course of an ordinary sunny day. The decomposition of the active chlorine also results in a drop in the desired pH level of the aqueous solution, thus requiring a pH adjustment with an alkali.

In U.S. Pat. No. 2,988,471, issued to Robert J. Fuchs et al on June 13, 1961, a method is disclosed for stabilizing aqueous solutions containing active chlorine against decomposition by ultraviolet light and by contact with iron and copper. The method disclosed therein involves adding to the solution cyanuric acid, ammelide or a salt of such compounds. The loss of active chlorine is substantially reduced when such materials are added to the solution in a weight concentration, expressed as the acid, which is greater than the weight concentration of available chlorine in the solution. The use of cyanuric acid to substantially reduce the loss of active chlorine in aqueous systems exposed to sunlight, for example, in swimming pools, has received wide commercial acceptance.

Although satisfactory results are achieved with the teachings of the prior art, those skilled in the art are interested in alternative materials which may be employed to stabilize the active chlorine in aqueous systems against decomposition upon exposure to ultraviolet light and/or when in contact with metals. Compounds which are easy to prepare and which offer cost/performance advantages would be of particular interest.

The object of the present invention is to provide a method for reducing the loss of active chlorine in aqueous systems upon exposure to ultraviolet light or by contact with metals such as iron, copper and aluminum employing compounds heretofore not disclosed for such use.

These and other objects will become apparent from the following detailed description.

SUMMARY OF THE INVENTION

In accordance with the present invention there is provided a method of stabilizing an aqueous solution containing active chlorine against the loss of active chlorine upon exposure to ultraviolet light or by contact with iron, copper or aluminum which comprises introducing into the solution a stabilizing amount of a radical represented by the structure

Compounds which may be employed to introduce the above-stated radical into the solution comprise compounds represented by the structure

wherein each R is individually hydrogen, an alkali metal or alkaline earth metal and R' is hydrogen, chlorine, an alkali metal or alkaline earth metal.

DESCRIPTION OF THE PREFERRED EMBODIMENTS

The term "active chlorine" when used herein means available-chlorine which has a valence of $+1$. As previously mentioned, it is known that active chlorine in an aqueous solution decomposes rapidly upon exposure to ultraviolet light and the result is the formation of chlorine with a valence of $-1$. The term "stabilization" as used herein means a reduction in the rate of loss of active chlorine.

It has been surprisingly found that the introduction of the radical represented by Structure I into aqueous solutions containing active chlorine has a stabilizing effect against the loss of active chlorine upon exposure to ultraviolet light and by contact with metals such as aluminum, iron or copper. Various compounds may be employed to introduce the radical of Structure I into the aqueous solution which is to be stabilized against the loss of active chlorine. Preferred compounds are those which do not introduce into the solution materials which are undesirable in view of the particular use for the solution. For example, it would not be desirable to introduce ammonium ions into swimming pool water.

Preferred compounds for use in the present invention comprise those represented by the structure

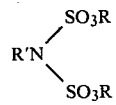

wherein each R is individually hydrogen, an alkali metal or alkaline earth metal, and R' is hydrogen, chlorine, an alkali metal or alkaline earth metal. One skilled in the art would recognize that alkali metals, e.g., sodium and potassium, are the metals of Group IA of the Periodic Table and alkaline earth metals, e.g., calcium, are metals of Group IIA of the Periodic Table. It is preferred that each R be the same. It is also preferred that R be an alkali metal, and even more preferred that each R be the same and be sodium or potassium. It is preferred that R' be hydrogen, an alkali metal or alkaline earth metal, and hydrogen is most preferred.

Certain of the compounds represented by the above Structure II may be preferred for stabilizing a particular solution because the compounds least affect the desired pH of the solution. Dipotassium and disodium imidodisulfate, i.e., the compounds represented by the above Structure II when R' is hydrogen and each R is potassium or sodium, respectively, are particularly preferred compounds for use in this invention and particularly for use in swimming pools.

Compounds represented by Structure II, which are imidodisulfonic acid and salts thereof, which are referred to as imidodisulfonates or imidodisulfates, can be prepared by various methods taught in the prior art. See, for example, J. W. Mellor, "A Comprehensive Treatise on Inorganic and Theoretical Chemistry", Longmans, Green & Co., Ltd., London (1931), Vol. VIII, pages 647 through 660, and references cited therein. More recently, the preparation of alkali metal imidobisulfates is described in U.S. Pat. No. 4,088,611, issued on May 9, 1978 to H. Suzuki et al. According to the procedure in that patent, diammonium imidobisulfate, $(NH_4SO_3)_2NH$, can be prepared by introducing ammonia gas and then sulfurous acid gas into an aqueous solution containing ammonium sulfite to obtain triammonium nitridotrisulfate and heating the obtained nitridotrisulfate in ammonia gas at about 250° C. under atmospheric pressure to ammonolyze and then heating to about 300° C. The diammonium imidobisulfate may then be treated with an alkali metal hydroxide to obtain an alkali metal imidobisulfate.

Certain of the chloroimidodisulfates, i.e., when R' is chlorine in Structure II and R is an alkali metal or alkaline earth metal, are known to be less stable as a solid than the corresponding imidodisulfates when R' is hydrogen, an alkali metal or alkaline earth metal. The stability of these chloroimidobisulfates is substantially improved if the compound is contained in an aqueous solution, and thus it is preferred to employ aqueous solutions of the chloroimidobisulfates in the present invention.

It is also recognized that the compounds represented by the Structure II may contain one or more molecules of water as water of hydration. These hydrated forms are considered to be equivalents of the compounds represented by the aforedescribed structure and are within the scope of the present invention.

The stability of active chlorine in aqueous solutions is affected by the pH of the solution. The method of the present invention is of particular interest when carried out at a pH from about 6 to about 9, for the aqueous solution including the stabilizer, although a stabilizing effect would be expected at pH values outside this range. Even more preferred is a pH from about 6.5 to about 8.5 for the aqueous solution including the stabilizer.

The method of the present invention is particularly useful for stabilizing swimming pool water containing active chlorine. In swimming pools, it is desired to maintain an available chlorine content of about 0.4 to about 5 ppm. A preferred pH range for the water is from about 6.8 to about 7.8.

The material which is employed to introduce the radical of Structure I into the aqueous solution may be added to the solution in any desired fashion, for example, by direct addition in a solid or liquid form. As previously mentioned, for certain compounds it may be preferred to employ dilute aqueous solutions containing compounds which comprise said radical. It is recognized that various other mixtures containing one or more compounds which would introduce the radical into the solution are possible.

The method of the present invention employs a stabilizing amount of the radicals of Structure I, that is, an amount which reduces the rate of loss of active chlorine in the aqueous solution upon exposure to ultraviolet light or by contact with metals such as iron, copper and aluminum. For purposes of the present invention, substantial stabilization is deemed to result if the amount of active chlorine lost in a two hour period is at least 10 percent less than the amount which would be lost under the same conditions for a corresponding solution having no stabilizer present.

The amount of stabilizing material employed will depend upon the concentration of the active chlorine in the aqueous solution. In general, it is preferred that the radical of Structure I be present in an amount by weight which is from about 0.3 to about 20 times the weight of the active chlorine present in the aqueous solution. More preferred is an amount by weight which is from about 1 to about 10 times the weight of the active chlorine in the aqueous solution. Compounds represented by Structure II are preferably employed in amounts which will provide the just-mentioned preferred amounts of the radical of Structure I. In general, the compounds of Structure II are preferably employed in an amount by weight which is from about 0.5 to about 25 times, more preferably about 1 to about 15 times, the weight of the active chlorine present in the aqueous solution.

Solutions which are stabilized by employing the method of the present invention are aqueous solutions containing active chlorine. Typical solutions are swimming pool water and sanitizing solutions. Various materials may be employed as a source of active chlorine in said solutions, for example, calcium or sodium hypochlorite and chlorinated isocyanurates. The solution being stabilized may contain various other materials depending on the particular use intended for said solution.

The following examples are given to illustrate the invention in detail. It is to be understood that the specific details given in the examples are not to be construed as limiting the scope of the invention. Unless otherwise specified, all parts, percentages and the like are by weight.

EXAMPLE I

Dipotassium imidodisulfate $(HN(SO_3K)_2)$ was prepared substantially according to the procedure described by P. Baumgarten, Ber., 69b, pp. 1929–1937 (1936). A solution of chlorine demand-free water containing approximately 5 ppm of active chlorine was prepared and buffered to maintain a pH at about 7.0, using sodium hypochlorite as a source of chlorine and sodium and potassium phosphate buffers.

To two samples of the chlorine-containing solution was added some of the dipotassium imidodisulfate (DKIS) at levels of 25 ppm and 50 ppm, respectively, based on the weight of the samples. The mixtures thus prepared and a sample of the water solution containing active chlorine were placed in open glass containers which were exposed to sunlight under outside conditions (temperature 22° to 31° C.). The active chlorine remaining in the samples at various time intervals was measured for each of the samples and results are presented in Table 1 in terms of percent active chlorine remaining at various elapsed times. Included for comparison purposes are typical data for the performance of cyanuric acid when added to like aqueous samples containing active chlorine.

TABLE 1

| SAMPLE | % Active Chlorine Remaining at Elapsed Times (Minutes) | | | | | | | |
|---|---|---|---|---|---|---|---|---|
| | 0 | 20 | 35 | 50 | 70 | 100 | 120 | 180 | 300 |
| A | 100% | 64 | 45 | 30 | 17 | 5 | 3 | — | — |
| B | 100% | 98 | 95 | — | 92 | 86 | — | 73 | — |
| C | 100% | 97 | 94 | 91 | 89 | 83 | 81 | 74 | 63 |
| D | 100% | 84 | 81 | 79 | 76 | 74 | 72 | 68 | — |
| E | 100% | 88 | 85 | 83 | 81 | 78 | 77 | 73 | — |

A-5 ppm active chlorine; no stabilizer
B-5 ppm active chlorine; 25 ppm DKIS
C-5 ppm active chlorine; 50 ppm DKIS
D-5 ppm active chlorine; 25 ppm cyanuric acid
E-5 ppm active chlorine; 50 ppm cyanuric acid

EXAMPLE II

A solution of chlorine demand-free water containing approximately 5 ppm active chlorine and having a pH of 7.2 was prepared by the procedure described in Example I, the active chlorine level and pH being typical for swimming pool water. Dipotassium imidosulfate which was prepared in Example I was added at different levels to samples of this aqueous solution.

The samples were placed in open glass jars and exposed to sunlight under outside conditions (temperature approximately 36° C.). The active chlorine present in each of the samples was measured at various time intervals and results are presented in Table 2 in terms of percent active chlorine remaining at various elapsed times.

TABLE 2

| AMOUNT OF DKIS | % Active Chlorine Remaining at Elapsed Times (Minutes) | | | | |
|---|---|---|---|---|---|
| | 0 | 20 | 60 | 100 | 180 |
| 0 | 100% | 69 | 38 | 20 | 4 |
| 5 ppm | 100% | 81 | 57 | 40 | 26 |
| 10 ppm | 100% | 86 | 69 | 57 | 44 |
| 15 ppm | 100% | 90 | 83 | 76 | 64 |
| 20 ppm | 100% | 97 | 94 | 89 | 80 |

EXAMPLE III

A solution of chlorine demand-free water containing approximately 10 ppm active chlorine and having a pH of 7.1 was prepared according to the procedure described in Example I. To three samples of this solution was added DKIS prepared in Example I at a 30 ppm level based on the weight of the sample. A different metal coupon was then placed in each of the samples and also in three samples of the chlorine-containing solution with no DKIS added. The samples were stored in the dark under ambient conditions. The active chlorine remaining in each of the samples was measured at various time intervals and results are reported in Table 3 in terms of percent active chlorine remaining at various elapsed times.

TABLE 3

| SAMPLES | % Active Chlorine Remaining at Elapsed Times | | | |
|---|---|---|---|---|
| | 0 | 2 Hours | 5.5 Hours | 17.5 Hours |
| Aluminum Coupon | | | | |

TABLE 3-continued

| SAMPLES | % Active Chlorine Remaining at Elapsed Times | | | |
|---|---|---|---|---|
| | 0 | 2 Hours | 5.5 Hours | 17.5 Hours |
| 0 DKIS | 100% | 79 | 68 | 34 |
| 30 ppm DKIS | 100% | 89 | 84 | 63 |
| Copper Coupon | | | | |
| 0 DKIS | 100% | 88 | 82 | 71 |
| 30 ppm DKIS | 100% | 95 | 89 | 85 |
| Iron Coupon | | | | |
| 0 DKIS | 100% | 82 | 50 | 5 |
| 30 ppm DKIS | 100% | 85 | 74 | 30 |

Although the invention has been described in terms of specific embodiments, it is to be understood that this is by way of illustration only, and that the invention is not necessarily limited thereto, since alternative embodiments within the present invention will become apparent to those skilled in the art.

What is claimed is:

1. A method of stabilizing an aqueous solution containing active chlorine as a sanitizing agent against the loss of active chlorine upon exosure to ultraviolet light or by contact with aluminum, copper or iron which comprises adding to the solution a stabilizing amount of a compound represented by the structure

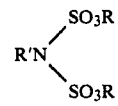

wherein each R is individually hydrogen, an alkali metal or alkaline earth metal and R' is hydrogen, chlorine, an alkali metal or alkaline earth metal.

2. A method in accordance with claim 1 carried out at a pH from about 6 to about 9.

3. A method in accordance with claim 2 wherein the pH is from about 6.5 to about 8.5.

4. A method in accordance with claim 2 wherein the compound is added in a weight amount which is from about 0.5 to about 25 times the weight of the active chlorine present in the aqueous solution.

5. A method in accordance with claim 1 wherein the compound is added in a weight amount which is from about 0.5 to about 25 times the weight of the active chlorine present in the aqueous solution.

6. A method in accordance with claim 1, 2, 3, 5 or 4 wherein R' is hydrogen.

7. A method in accordance with claim 6 wherein each R is individually sodium or potassium.

8. A method of stabilizing an aqueous solution containing active chlorine as a sanitizing agent against the loss of active chlorine upon exposure to ultraviolet light or by contact with aluminum, copper or iron which comprises adding to the solution a compound which is dipotassium imidodisulfate in a weight amount which is from about 1 to about 15 times the weight of the active chlorine present in the aqueous solution provided the pH of the solution including the dipotassium imidodisulfate is from about 6.5 to about 8.5.

9. A method of stabilizing an aqueous solution containing active chlorine as a sanitizing agent against the loss of active chlorine upon exposure to ultraviolet light or by contact with aluminum, copper or iron which comprises adding to the solution a compound which is disodium imidodisulfate in a weight amount which is from about 1 to about 15 times the weight of the active chlorine present in the aqueous solution provided the pH of the solution including the disodium imidodisulfate is from about 6.5 to about 8.5.

* * * * *